(12) United States Patent
Sluis

(10) Patent No.: US 8,500,890 B2
(45) Date of Patent: Aug. 6, 2013

(54) AIR CHANNEL WITH INTEGRATED ODOR ABSORBING ELEMENT

(75) Inventor: Daniel Vander Sluis, Rochester Hills, MI (US)

(73) Assignee: Faurecia Interior Systems, Inc., Auburn Hills, MI (US)

( * ) Notice: Subject to any disclaimer, the term of this patent is extended or adjusted under 35 U.S.C. 154(b) by 211 days.

(21) Appl. No.: 13/037,439

(22) Filed: Mar. 1, 2011

(65) Prior Publication Data

US 2012/0222559 A1    Sep. 6, 2012

(51) Int. Cl.
*B01D 53/02*  (2006.01)
(52) U.S. Cl.
USPC ................................. 96/154; 96/90
(58) Field of Classification Search
USPC .................................... 96/108, 154
See application file for complete search history.

(56) References Cited

U.S. PATENT DOCUMENTS

| | | | | |
|---|---|---|---|---|
| 3,857,732 A * | 12/1974 | Yoshino | | 427/389.9 |
| 3,925,021 A * | 12/1975 | Yoshino et al. | | 96/118 |
| 4,007,875 A * | 2/1977 | Stolz et al. | | 237/12.3 A |
| 4,013,566 A * | 3/1977 | Taylor | | 502/62 |
| 4,464,260 A * | 8/1984 | Duneau | | 210/232 |
| 4,906,263 A * | 3/1990 | von Blucher et al. | | 96/135 |
| 5,338,253 A * | 8/1994 | Damsohn et al. | | 454/158 |
| 5,350,443 A * | 9/1994 | von Blucher et al. | | 96/135 |
| 5,350,444 A * | 9/1994 | Gould et al. | | 96/154 |
| 5,603,753 A * | 2/1997 | Krull et al. | | 96/121 |
| 5,616,169 A * | 4/1997 | de Ruiter et al. | | 95/90 |
| 5,810,896 A * | 9/1998 | Clemens | | 55/385.3 |
| 5,876,277 A | 3/1999 | Uemura et al. | | |
| 5,938,523 A * | 8/1999 | Khelifa et al. | | 454/156 |
| 6,019,676 A * | 2/2000 | Kim | | 454/155 |
| 6,120,584 A * | 9/2000 | Sakata et al. | | 96/135 |
| 6,280,824 B1 * | 8/2001 | Insley et al. | | 428/172 |
| 6,352,579 B1 * | 3/2002 | Hirata et al. | | 96/134 |
| 6,849,107 B1 * | 2/2005 | Huffman | | 96/224 |
| 6,905,536 B2 * | 6/2005 | Wright | | 96/134 |
| 7,407,533 B2 * | 8/2008 | Steins | | 96/134 |
| 7,591,720 B2 * | 9/2009 | Kim et al. | | 454/252 |
| 7,621,372 B2 * | 11/2009 | Yamaura et al. | | 181/229 |
| 7,789,927 B2 * | 9/2010 | Tramontina et al. | | 55/491 |
| 2004/0055469 A1 * | 3/2004 | Kroculick | | 96/134 |
| 2006/0107835 A1 * | 5/2006 | Heilmann et al. | | 96/108 |
| 2009/0282984 A1 * | 11/2009 | Lee et al. | | 96/140 |

FOREIGN PATENT DOCUMENTS

| | | |
|---|---|---|
| JP | 2008132844 A | 6/2008 |
| WO | 2010074311 A1 | 7/2010 |

* cited by examiner

*Primary Examiner* — Christopher P Jones
(74) *Attorney, Agent, or Firm* — Matthew B. Dernier, Esq.; Gibson & Dernier LLP

(57) ABSTRACT

An odor absorption component is fitted to a duct in a manner that does not obstruct fluid flow through the duct while simultaneously facilitating absorption of odors from a fluid flowing within the duct. The absorbing component comprises one or more carrier structures that support a fabric/textile treated with an odor absorption coating. In one position, the carrier structures can be placed on the wall of the duct such that a plane of the support structure is parallel to and in physical contact with the fluid flow within the duct. The carrier structures may also be placed in another position within the duct such that at least two surfaces of the carrier structure that extend in a longitudinal direction along its length are parallel to and in the path of the fluid flow within the duct.

26 Claims, 10 Drawing Sheets

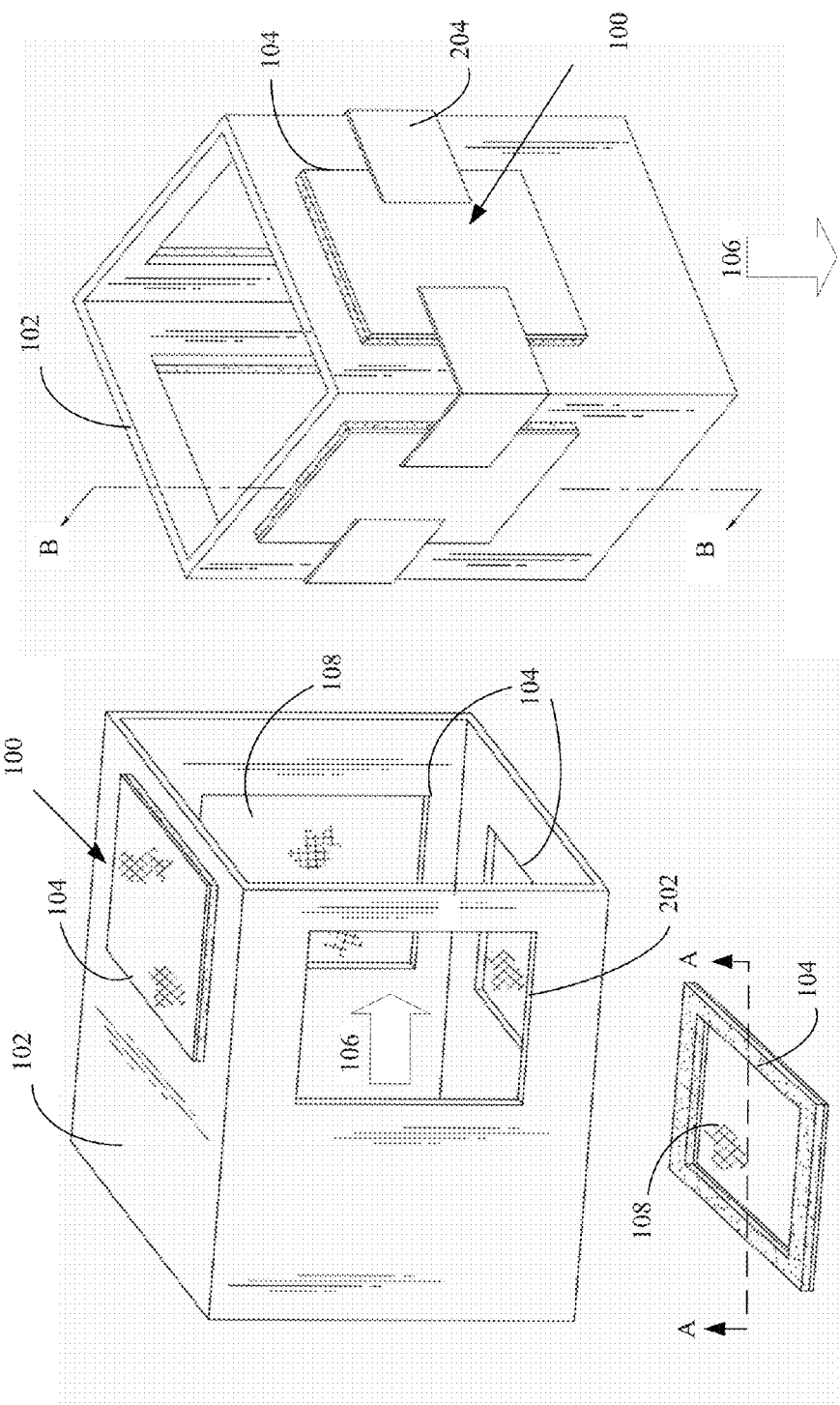

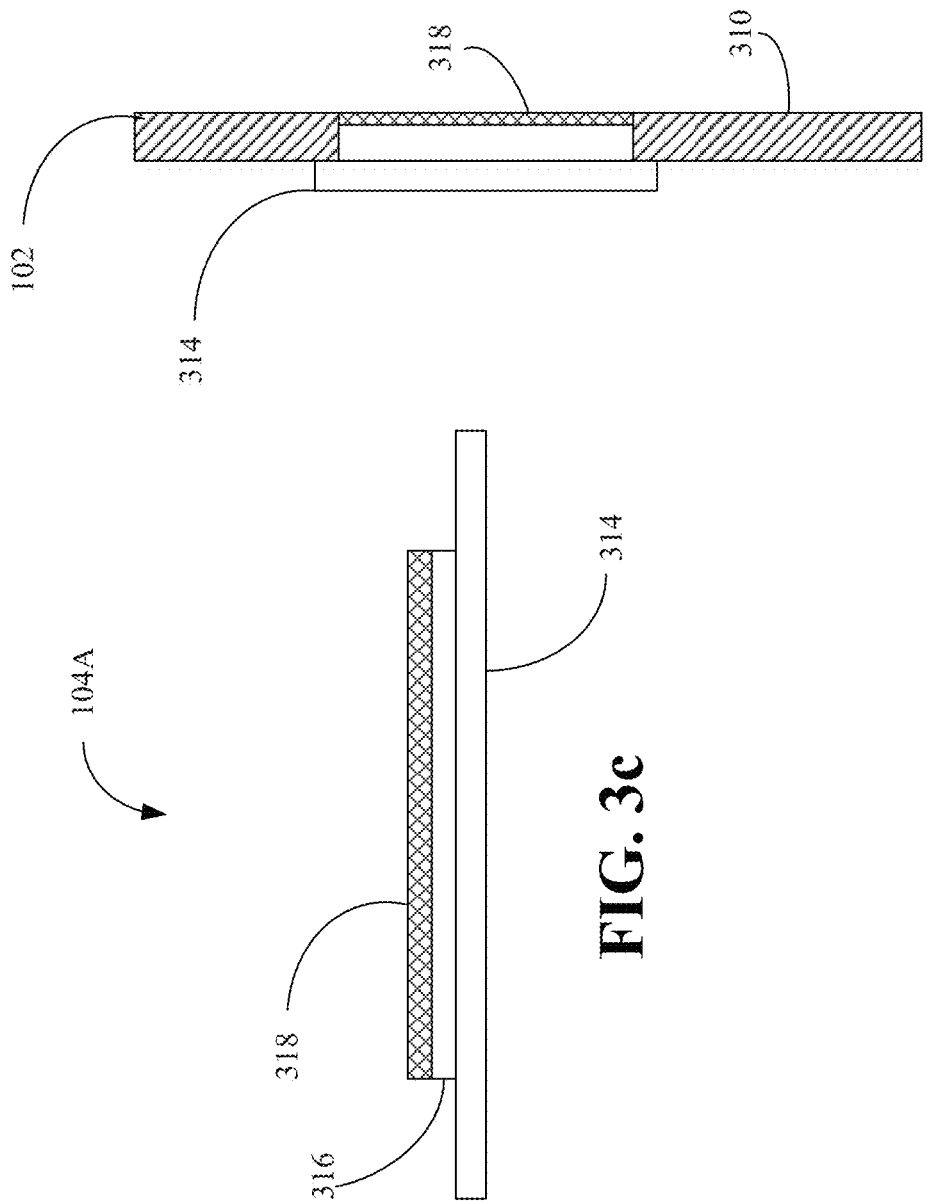

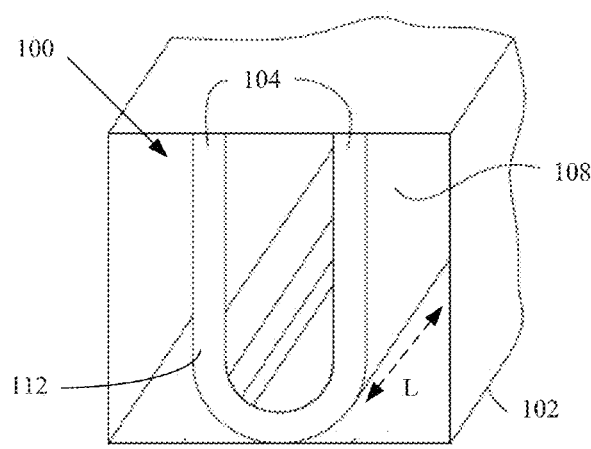
FIG. 5a
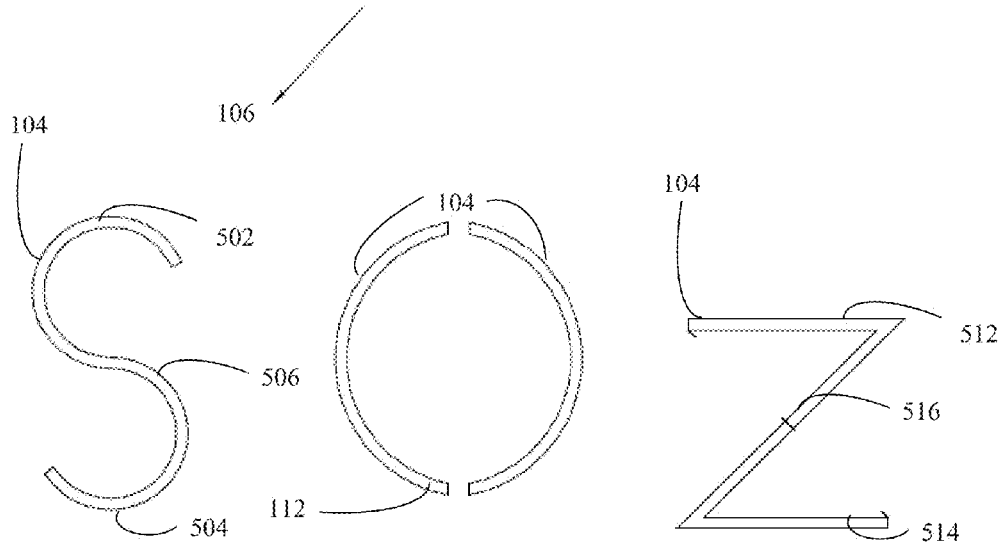
FIG. 5b  FIG. 5c  FIG. 5d

AIR CHANNEL WITH INTEGRATED ODOR ABSORBING ELEMENT

FIELD OF THE INVENTION

The present invention relates generally to deodorizing systems and in particular, to deodorizing a vehicle interior without impeding air flow.

BACKGROUND OF THE INVENTION

Automotive HVAC (Heating, Ventilating and Air Conditioning) systems are designed to provide optimum comfort to passengers in a vehicle. These systems generally include a vent to let fresh air into the vehicle which may be closed when so desired. For example, when the vehicle travels through an area where the outside air has bad odors present, a passenger in the vehicle can close the fresh air vent in order to limit the outside air from entering the passenger compartment. In this case, the HVAC system of the vehicle re-circulates the interior air within the vehicle.

However, it may not be desirable to re-circulate interior air within a vehicle for extended periods of time as there are occasions when outside air ventilation will allow for more comfortable interior temperatures without the use of AC (Air Conditioning) in addition to improving the overall efficiency of the HVAC system. Hence, deodorizing filters currently manufactured in the vehicle HVAC systems or aftermarket units added to the vehicle interior by the user offer alternative means for dealing with objectionable odors. However, many of the current technologies employed in traditional air "filter media" (mechanical or electrostatic), do not effectively remove odors introduced into the ventilated and ducted air in a vehicle HVAC system. Generally, the filter media is oriented at 90 degrees to the flow of air, thus restricting the flow rate and the effective pressure of the air out of the register openings which in turn limits the intended time to comfort of the vehicle occupants. Known techniques for filtering and/or purifying the "air" in vehicle cabin environments (specifically applications for instrument panel or console applications) involve the use of one of the following technologies: filter media (textile fibers and/or electrostatic methods), Ionizers, Ozone Generator or a UV Photocatalytic Air Purifier.

However, the air filtering and odor absorbing methods mentioned above have drawbacks and limitations, namely those of cost, package-ability (i.e., restricting airflow) and overall system complexity, such as, requiring electrical power routed to the "air" purifying device. Moreover, ozone generators, air purifiers and ionizers are very expensive when compared to passive carbon based air filters and media filters (e.g., 3M, etc.). Also, such filters typically do not effectively absorb odors, as they are primarily designed to remove micro-particle substances from the passing air enabled by traditional electrostatic processes. Hence, a design for air deodorizing systems should effectively deodorize air without impeding air flow.

SUMMARY OF THE INVENTION

In accordance with various aspects described herein, a deodorizing system that effectively deodorizes the air without obstructing the air flow or reducing air pressure is disclosed.

In one aspect, the deodorizing system comprises at least one absorption component that absorbs odors from a fluid flowing through a duct/channel housing. The absorption component comprises at least one absorption surface that extends in a longitudinal direction and facilitates the odor absorption. The absorption component is configured to be arranged with respect to the channel housing such that the longitudinal direction of the absorption surface is substantially parallel to the fluid flow. The absorption component further comprises at least one carrier structure with a deodorant fabric impregnated with an odor absorbing coating that forms the absorption surface. In different aspects, the deodorant fabric is molded into or bonded to the carrier structure.

In accordance with a more detailed aspect, the absorption component can comprise a plurality of such carrier structures. Each of the carrier structures can be affixed to one of a plurality of adjacent sides of the channel housing in a manner such that fluid particles at a peripheral portion of the fluid flow are in physical contact with the deodorant fabric. In a further aspect, the carrier structure is affixed to the channel housing such that the absorption surface comprising the deodorant fabric in contact with the fluid flow is flush with an inner surface of the channel housing. The carrier structure can include means, such as foam seals, for fixing it to the channel housing. The plurality of carrier structures can be interconnected to each other thereby creating a band that surrounds at least a portion of the fluid flow such that only one side of the carrier structures bearing the deodorant fabric is in physical contact with the fluid flow.

In one aspect, the absorption component is arranged in a path of the fluid flow within the channel housing. In this aspect also, the absorbing component can comprise a plurality of carrier frames arranged parallel to each other with gaps therebetween. Therefore, this arrangement of the absorption component also facilitates odor absorption without hindering fluid flow. Combinations of the aforementioned arrangements of carrier structures that facilitate efficient odor absorption without obstructing air flow are also possible as further detailed infra.

The carrier structure is primarily a support structure made up of material such as molded plastic configured into different shapes facilitating design flexibility and air flow efficiency of the absorption component profile as needed. In one aspect, the carrier structure is configured to be a continuous sheet of material with the deodorant fabric affixed to at least one side of the sheet while in another aspect the carrier structure can be configured as a frame with an aperture that is covered by the deodorant fabric. Furthermore, the carrier structure with the absorption surface including the deodorant fabric could additionally be configured into various planar and/or arcuate profiles as needed to improve package or manufacturing efficiency.

A deodorizing filter with the absorption component thus constructed can be placed at various positions along a vehicle HVAC system in order to facilitate deodorizing the vehicle interior without obstructing air flow. A preferred position in the HVAC system for the deodorizing filter with carrier structure unit would be in the main panel air ducts assembly just prior to the exit of the air through the air register apertures. This position allows for the air to stay in contact with the odor absorbing coating for a longer time as the air flow is potentially at it's slowest in this position. In addition, placement of the absorption component in this position allows it to "straighten the air" thereby enhancing the air flow directionality as it exits the register. Further advantages gained by placing the absorption component just prior to the outlet of the air vent include potential cost savings with regard to the air register itself as it may reduce the number of required vanes to some extent.

BRIEF DESCRIPTION OF THE DRAWINGS

FIG. 2a illustrates placement of the absorption component on a duct in accordance with one embodiment of the invention.

FIG. 2b illustrates placement of the absorption component on a duct in another view in accordance with one embodiment of the invention.

FIG. 3c shows a cross sectional view of the odor absorption component along the line A-A shown in FIG. 2a in accordance one embodiment of the invention.

FIG. 3d shows a cross sectional view of the odor absorption component on the duct along the line B-B shown in FIG. 2b in accordance one embodiment of the invention.

FIGS. 5a-5d show various profiles that may be used for the absorption component in accordance with different embodiments.

DETAILED DESCRIPTION OF THE EMBODIMENTS

In the following description, for purposes of explanation, specific numbers, materials and configurations are set forth to provide a thorough understanding of the invention. It will be apparent to one having ordinary skill in the art that the invention may be practiced without these specific details. In some instances, well-known features may be omitted or simplified so as not to obscure the present invention.

Figure 1B:
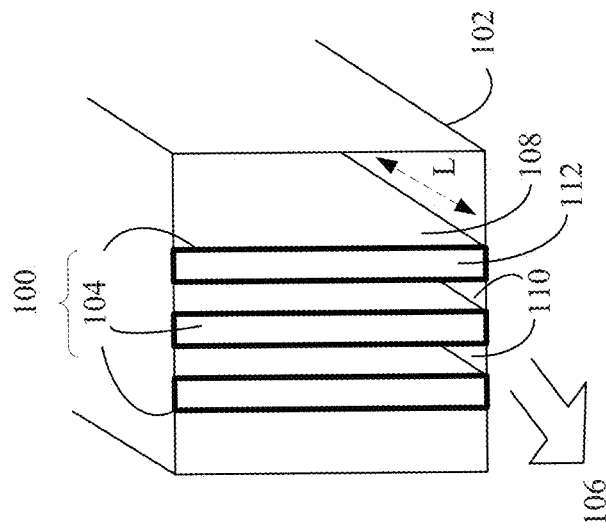
FIG. 1b illustrates an absorption component in accordance with an embodiment of the present invention.
Figure 1A:
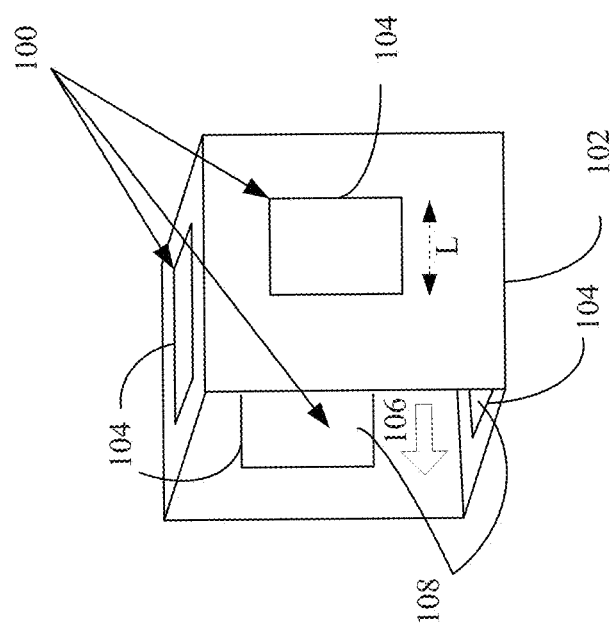
FIG. 1a illustrates an absorption component in accordance with an embodiment of the present invention.

Turning now to the drawings, wherein like reference numerals denote like or corresponding parts throughout the drawings, FIG. 1a shows a schematic view of an arrangement of an absorption component 100 in accordance with an embodiment of the present invention. The absorption component 100 is configured to be placed with respect to a channel/duct 102 carrying a fluid such that at least one absorption surface 108 of the absorption component 100 is parallel to and away from a path of the fluid flow 106 within the duct 102 while simultaneously maintaining physical contact with at least the particles at a periphery of the fluid flow 106. As seen from FIG. 1a, the absorption component 100 may have one or a plurality of carrier structures 104 that are configured to be placed on corresponding apertures (not shown) of the duct 102 such that the structures 104 cover the apertures and fluid particles at least at a periphery of the fluid flow 106 will be in physical contact with the one or more absorption surfaces 108 extending along the length L of the carrier structures 104. Although a plurality of carrier structures 104 are shown herein, it may be appreciated that the absorption component 100 may include only one carrier structure 104 covering one aperture within the air duct 102. Thus, the absorption component 100 facilitates absorbing odors from the fluid flowing within the duct 102 without impeding the fluid flow 106. The absorption component 100 may be placed at the inlet, at the outlet, or at an intermediate position of a fluid circulation system to facilitate the odor absorption.

FIG. 1b shows a schematic view of another arrangement of the absorption component 100 with respect to the duct 102. In accordance with this embodiment, the absorption component 100 is placed in the path of the fluid flow 106 such that at least one absorption surface 108 of the absorption component 100 is parallel to the fluid flow 106. More particularly, the absorption surface 108 extends in the longitudinal direction parallel to a length L of a carrier structure 104 that is comprised within the absorption component 100. Therefore, in accordance with this aspect, the absorption component 100 is arranged with respect to the duct 102 such that the longitudinal direction or the length L of the carrier structure 104 is parallel to the fluid flow 106 as shown in FIG. 1b. In this aspect, the entire surface area of the absorption surface 108 is parallel to the fluid flow while a minimum quantum of the two-dimensional surface area 112 of the carrier structure 104 is transverse to the fluid flow 106. In accordance with a further aspect of this embodiment a plurality of such carrier structures 104 that make up the absorption component 100 are placed within the fluid flow 106 with interstitial spaces 110 (gaps) therebetween. Based on the configuration of the absorption component 100 as discussed in further detail infra, such arrangement of the absorption component 100 can increase the surface area of the carrier structures 104 exposed to the fluid flow 106 within the duct 102, thereby facilitating a more efficient absorption of odors from the fluid.

Thus, the absorption component 100 in accordance with the embodiments as described herein is mounted in line with the fluid flow 106. An odor reducing fabric/textile element of the absorption component 100 is not oriented perpendicular to the flow of air/fluid (unlike foam or other electrostatic substrate filters) to eliminate odors. Therefore it does not restrict air/fluid flow or reduce air/fluid pressure in the air channels or out of the registers.

FIG. 2a shows placement of the absorption component 100 on a duct 102 parallel to the fluid flow 106 in accordance with one embodiment of the invention. FIG. 2a illustrates a view of the inner part of the duct 102 with the absorption component 100 placed thereon covering one or more apertures 202 in the duct 102. In accordance with this embodiment, the absorption component 100 comprises a plurality of carrier structures 104 affixed to a the duct 102 such that the corresponding inner surfaces 108 of the carrier structures 104 overlie a plurality of the apertures 202 and thus are in contact with the fluid flowing through the duct 102. It may be appreciated that although the duct 102 is shown to have a rectangular cross section, this is not necessary. Indeed, the duct 102 may have alternate configurations, such as a cylindrical configuration, where the absorption component 100 can be modified accordingly and used as described herein.

FIG. 2b illustrates another embodiment of the absorption component 100 that forms a band around the air duct 102. In this aspect, a series of carrier structures 104 are interconnected to each other via connecting elements 204 thereby creating a band-like construction that is placed around the duct 102 and wherein each of the carrier structures 104 is aligned with corresponding apertures 202 in the duct 102. The connecting elements 204 can be made of suitable materials, such as fabric, flexible plastic etc. that are strong enough to hold the carrier structures 104 while being flexible enough to allow the band-like construction formed of the carrier structures 104 to firmly wrap around the duct 102. The carrier structures 104 may also be affixed to the duct 102 such that they cover the apertures 202 in addition to being interconnected to each other. The absorption component 100 may thus comprise of two or more structures 104 connected together to form a band that at least partially covers the fluid flow within the duct 102. FIG. 2b particularly shows four such structures interconnected to each other thereby forming a band that surrounds the fluid flow 106 in the duct 102 and hence facilitating more efficient odor absorption.

Figure 3B:
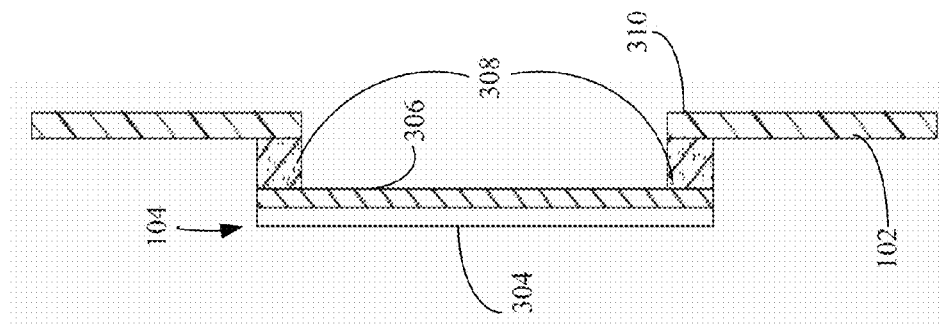
FIG. 3b shows a cross sectional view of the odor absorption component on the duct along the line B-B shown in FIG. 2b in accordance with one embodiment of the invention.
Figure 3A:
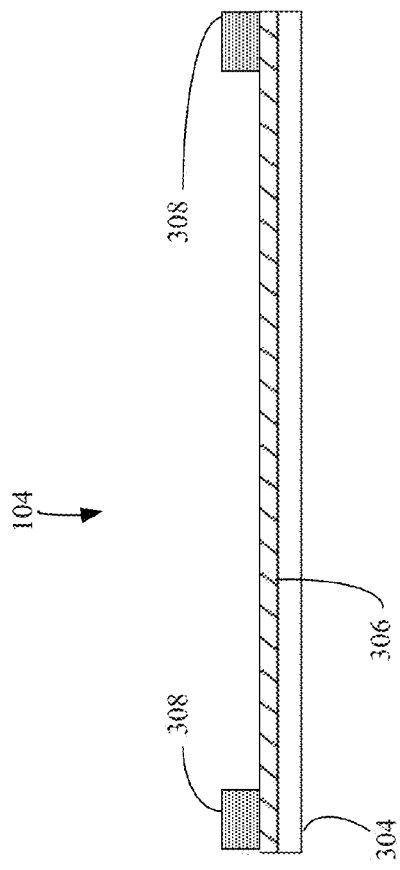
FIG. 3a shows a cross sectional view of the odor absorption component along the line A-A shown in FIG. 2a in accordance with one embodiment of the invention.

FIG. 3a is a cross sectional view of one of the carrier structures 104 of the odor absorption component 100 along the line A-A shown in FIG. 2a in accordance with one embodiment. The carrier structure 104 in accordance with this embodiment, comprises a base 304 primarily configured from a continuous sheet of material such as plastic, etc., with a textile/fabric 306 molded on or bonded to one extended surface side of the base 304 which will be in contact with the fluid flow via the aperture 202. The fabric 306 is coated with a deodorant in order to facilitate odor absorption. The fabric/textile 306, treated with the deodorant (e.g., an odor reducing solution), mostly acts as a functional carrier of the odor reducing solution so that the fabric/textile can vary based on the requirements of the application. This will lower the functional cost of the absorption component 100 versus traditional odor reducing methods that are currently available.

The fabric 306 can be a deodorant fiber product having a deodorization speed that allows rapid deodorization of various bad odors and having a high deodorizing rate, such as those manufactured by Seiren Co., Ltd., of Japan. For example, the deodorant fiber product may be formed with inorganic porous crystals supported on the surface and in the interior of cellulose fibers. It is characterized by having on the surface and/or in the interior one type or at least two types of deodorant substances selected from a group comprised of a compound of silicon dioxide and zinc oxide, a compound of amorphous silica and/or silica alumina and phyllosiliccate and or aluminum phyllosilicate, a polyhydrazide compound, polycarboxylic acid and/or polycarboxylate and polyphenol. The surface of the fabric 306 may be substantially smooth or it may be corrugated in accordance with different embodiments. The structure 302 may also include means, such as foam seals 308, glue or other mechanical means for fixing it to the duct 102.

FIG. 3b is a cross sectional view of one of the carrier structures 104 of the odor absorption component 100 affixed to the duct 102 along the line B-B shown in FIG. 2b. As shown in FIG. 3b, the structure 104 is affixed to the duct 102 by means of foam seals 308. The continuous sheet of material that forms the base 304, in conjunction with the foam seals 308 prevents the fluid from escaping from a junction of the structure 104 and the duct 102.

In accordance with the embodiments disclosed herein and shown in FIG. 3b, the fabric surface 306 is slightly recessed from the inner surface 310 of the duct 102. Hence, another embodiment of the carrier structure 104 of the absorption component 100 can also be contemplated wherein the fabric 306 is flush with the inner surface 310 of the duct 102. FIG. 3c shows a cross sectional view of a carrier structure 104A of the absorption component 100 in accordance with one such embodiment that is configured to have a surface bearing the fabric 318 to be flush with the inner surface 310 of the duct 102. The structure 104A in accordance with this embodiment has a base 314 with a slightly raised platform 316 bearing the deodorant coated fabric 318 thereon.

FIG. 3d shows a cross sectional view of the structure 104A shown in FIG. 3c affixed to the duct 102. The height of the platform 316 of the structure 104 can be such that the fabric 318 is flush with the inner surface 310. The base 314 also facilitates attaching the structure 104 to the duct 102 by various means for attachment such as foam seals, glue, mechanical fixtures etc.

Figure 4A:
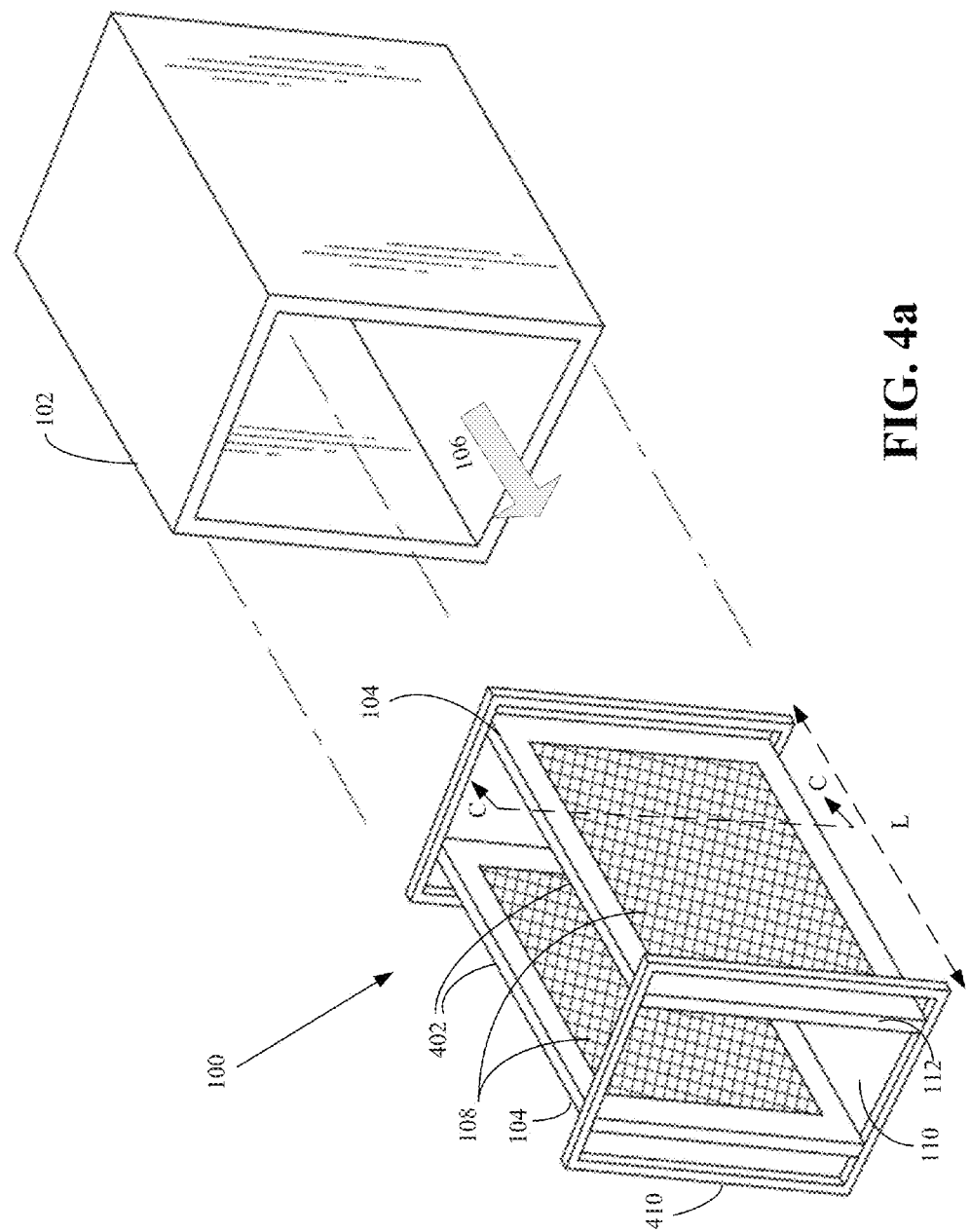
FIG. 4a shows placement of the absorption component in a duct in accordance with another embodiment of the present invention.

FIG. 4a shows an arrangement of the odor absorption component 100 in accordance with another aspect. In this embodiment, the absorption component 100 can comprise one or more carrier structures 104 placed within the duct 102 in the path of the fluid flow such that the two surfaces 402 (not shown), 108 of the carrier structure 104 extending in a longitudinal direction along the length L of the carrier structure 104 are both parallel to, and in contact with, the fluid flow 106. If the absorption component 100 is comprised of more than one carrier structure 104, the structures 104 are separated by gaps 110 that facilitate the fluid to flow between them. Thus, the fluid comes into contact with at least one side of the carrier structure 104 that bears the deodorant coated fabric, for example, the absorption surface 108, thereby facilitating odor absorption. In accordance with further embodiments that will be described in greater detail infra, one or both sides 402 and 108 of the structure 104 in this embodiment may comprise the deodorant coated fabric and may hence act as the absorption surfaces.

In accordance with different aspects, the structure(s) 104 may either fit snugly into the duct 102 or may comprise attachment means 410 that facilitate attachment of the structure(s) 104 to the duct 102. In one particular embodiment illustrated in FIG. 4a, the plurality of carrier structures 104 are fitted into a molded plastic frame 410 such that they maintain gaps 110 therebetween. The plastic frame 410 is configured to fit snugly into the duct 102.

Figure 4B:
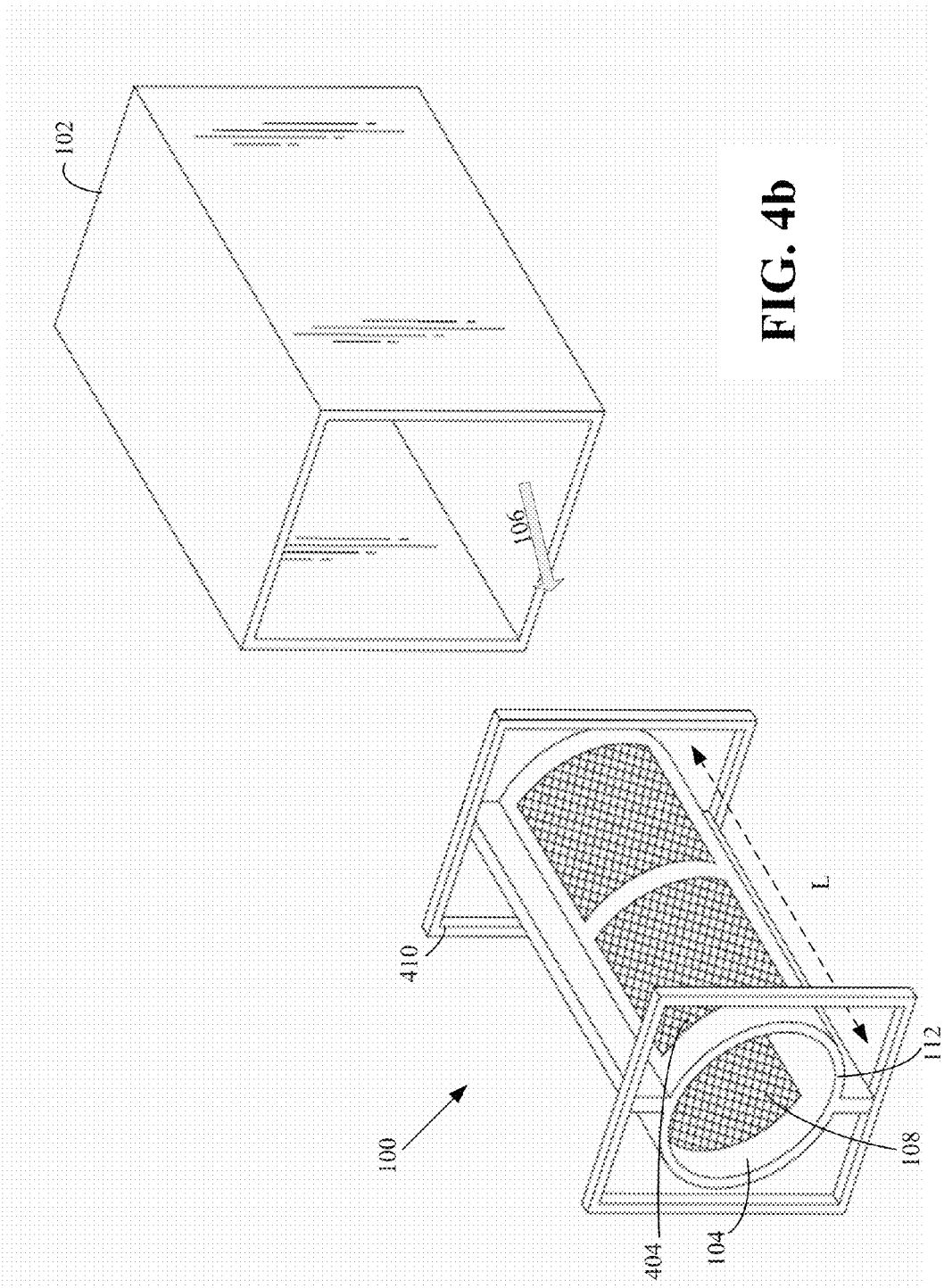
FIG. 4b shows placement of the absorption component in a duct in accordance with yet another embodiment of the present invention.

FIG. 4b shows an arrangement of the odor absorption component 100 in accordance with yet another aspect. In this embodiment, the absorption component 100 comprises a carrier structure 104 configured as a circular duct with one or more absorption surfaces included on at least one of the inner surface 108 or the outer surface 404 which extend in a longitudinal direction parallel to the length L of the carrier structure 104. In this aspect, the absorption component 100 is arranged such that the longitudinal direction is parallel to the fluid flow 106 and that a minimum quantum of surface area 112 is transverse to the fluid flow 106. In the illustrated embodiment, all of the surface area of the inner and outer surfaces 108, 404 is parallel to the fluid flow 106, while none of the surface area thereof is transverse to the fluid flow 106. In alternative embodiments, the contour of the surfaces 108, 404 may be such that some fraction of the surface area is transverse to the fluid flow 106. It is desirable, however, to minimize such transverse fraction and maximize the parallel fraction in order to achieve high flow rates.

In accordance with different aspects, the structure 104 may either fit snugly into the duct 102 such that the outer surface 404 of the carrier structure 104 is in contact with the duct 102 or the carrier structure 104 may further comprise attachment means 410 that facilitate attachment of the structure 104 to the duct 102.

In a further aspect, the carrier structure 104 can be configured to have different profiles such as planar or circular profiles as shown FIGS. 4a, 4b. FIGS. 5a-5d show other profiles that may be employed for the carrier structure 104.

FIG. 5a shows an absorption component 100 fitted to a duct 102 with a carrier structure 104. In accordance with this aspect, the carrier structure 104 is 'U' shaped having at least one absorption surface 108 extending in a longitudinal direction parallel to the length 'L' of the carrier structure 104. As seen from FIG. 5a, a minimum quantum of surface area (only that of surface 112) extends transverse to the fluid flow 106. FIG. 5a shows the absorption component 100 with only one carrier structure 104. It may be appreciated that a plurality of such carrier structures 104 can be placed within a duct 102 with interstitial spaces therebetween.

FIG. 5b shows a profile of a carrier structure 104 used in the absorption component 100 in accordance with another aspect wherein the carrier structure 104 is 'S' shaped. As mentioned supra, the carrier structure 104 may either fit snugly into the duct 102 or it may comprise further attachment means (not shown) to facilitate attachment of the carrier structure 104 to the duct 102. If the carrier structure 104 is configured to couple directly to the interior of the duct then some portions of the absorption surface will be in the path of the fluid flow. For example, the part of the absorption surface along the upper curve 502 and the part of the absorption surface along the lower curve 504 will not be in the fluid flow 106 while the part of the absorption surface extending along the central section 506 of the carrier structure 104 will be in the path of the fluid flow 106 in accordance with the different orientations of the absorption component 100 as discussed herein. In either case, the absorption component 100 will be oriented such that the absorption surface 108 will extend in a longitudinal direction which is parallel to the fluid flow 106.

FIG. 5c shows the profile two carrier structures 104 of a circular absorption component 100 wherein each carrier structure is configured to have an arcuate profile in accordance with another embodiment. As further shown in FIG. 5c, a minimum quantum of surface area (only that of surface 112) will be transverse to the direction of the fluid flow 106.

FIG. 5d shows a profile of a carrier structure 104 in accordance with another aspect wherein the carrier structure 104 is 'Z' shaped. As mentioned supra, the carrier structure 104 may either fit snugly into the duct 102 or it may comprise further attachment means (not shown) to facilitate attachment of the carrier structure 104 to the duct 102. Again, as discussed supra, the part of the absorption surface along the upper segment 512 and the part of the absorption surface along the lower segment 514 of the carrier structure 102 may be out of a path of the fluid flow (in order to connect to the interior of the duct 102), while the part of the absorption surface extending along the central section 516 of the carrier structure 104 will be in the path of the fluid flow 106 in accordance with the different orientations of the absorption component 100 as discussed herein.

In addition to its shape, the carrier structure 104 can also be configured in different ways in accordance with different embodiments. For example, the carrier structure 104 can have a planar structure made up of a continuous sheet of material with the odor absorption fabric 306 molded to one or both sides of the sheet material. In another aspect, the carrier structure can be configured to have an aperture that is covered by one or more sheets of the odor absorption fabric.

Figure 6A:
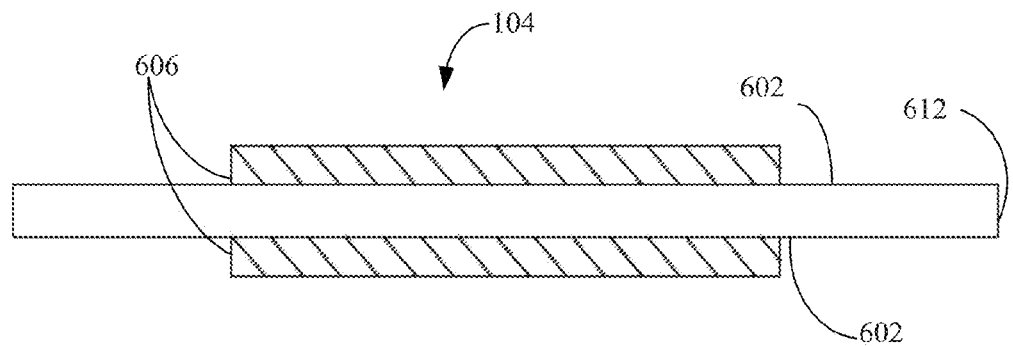
FIG. 6a shows a cross sectional view of the absorption component in one aspect.

Accordingly, FIG. 6a is a cross sectional view of the structure 104 taken along the line C-C of FIG. 4a. In accordance with this embodiment, the structure 104 comprises a base 612 formed from a continuous sheet of material, such as, plastic, etc. and having two surfaces 602, each bearing a deodorant coated fabric 606 thereon to facilitate odor absorption. The structure 104 may either be sized to fit snugly into the duct 102 in the path of the fluid flow 106 or may comprise attachment means, such as those described supra, for attaching it to the upper and lower inner surfaces of the duct 102. It may be appreciated that it is not necessary that the structure 104 when being placed in the path of the fluid flow should have the deodorant coated fabric 506 on both the sides 602 of the extended surface as shown herein. In accordance with different aspects, the carrier structure 104 bearing the deodorant coated fabric 606 on only one side of the extended surface as shown in FIG. 3a or 3c may also be placed in the path of the fluid flow 106 to facilitate odor absorption.

Figure 6B:
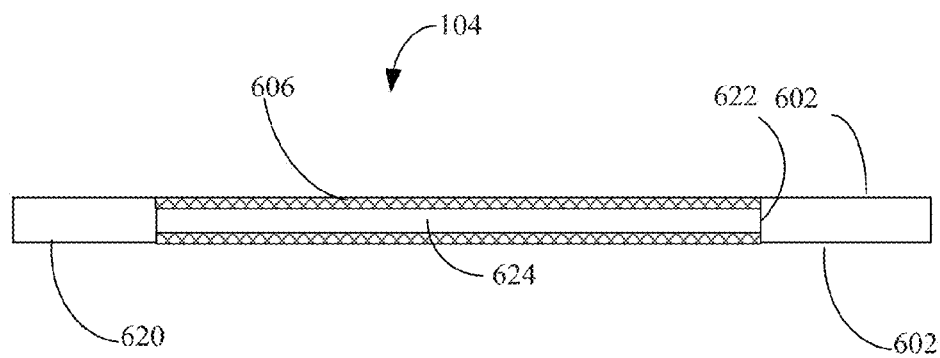
FIG. 6b shows a cross sectional view of the absorption component in one aspect.

FIG. 6b is a cross sectional view of the structure 104 along the line C-C in FIG. 4a in accordance with yet another embodiment. In accordance with this aspect, the structure 104 comprises a base 620 with two extended surfaces 602 having an aperture 622. Thus, the base 620 forms a frame that receives the deodorant fabric 606 on at least one side of the aperture 622. In the embodiment illustrated in FIG. 6b the deodorant fabric 606 is attached to both sides of the frame 620 with a gap 624 therebetween. This embodiment of the carrier structure 104 facilitates better odor absorption due to the increase in the surface area of the fabric 606 exposed to the fluid. However, it does not impede fluid flow despite being placed in the path of the fluid as the extended surfaces 602 are parallel to the fluid flow 106. Depending on the fluid permeation achieved through the odor reducing element described herein, the fabric/textile could be more porous than any traditional filter media. It will also allow placement of the absorption component at 90 degrees to airflow, if needed, with less restriction than traditional filter media currently existing.

Figure 6C:
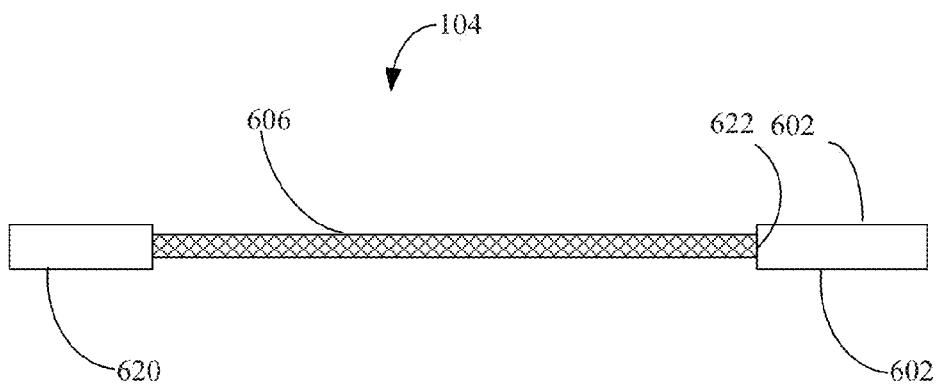
FIG. 6c shows a cross sectional view of the absorption component in one aspect.

FIG. 6c is a cross sectional view of the structure 104 along the line C-C in FIG. 4a in accordance with yet another embodiment. In accordance with this aspect, the structure 104 comprises a base 620 with two extended surfaces 602 and having an aperture 622. Thus, the base 620 forms a frame that receives the deodorant fabric 606 within the aperture 622. In accordance with further embodiments, one or both sides of the fabric 606 may be coated with an odor absorbing coating based on the requirements of an application.

Figure 7:
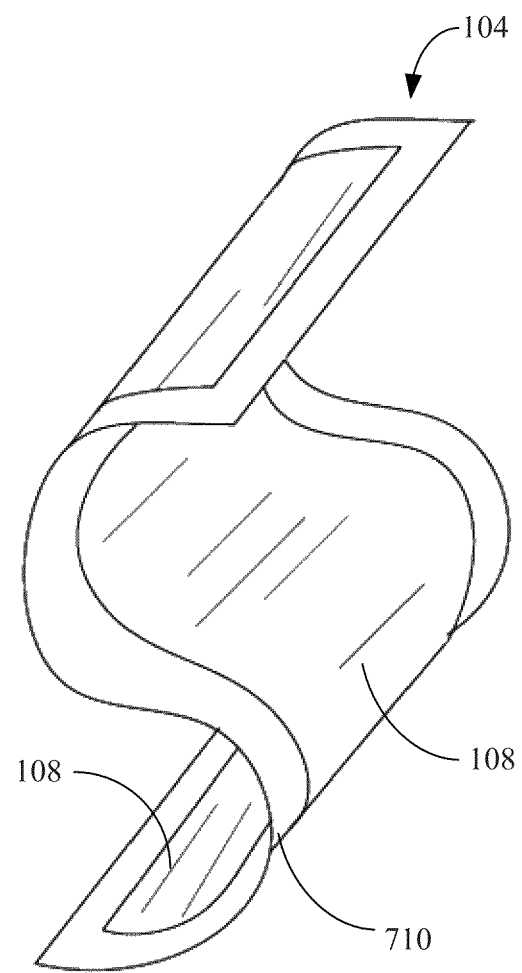
FIG. 7 shows a schematic diagram of a carrier structure having an 'S' shaped profile bearing two absorption surfaces on either side in accordance with an embodiment of the invention.

FIGS. 6a-6c show only the cross sectional views of the carrier structures 104 with a planar shape. However, it may be appreciated that the carrier structure 104 can be configured in accordance with various combinations of different profiles with the shapes such as circular, arcuate, 'U', 'S', etc., as shown in FIGS. 5a-5d. For example, FIG. 7 shows an 'S' shaped carrier structure 104 made up of a continuous sheet material 710 configured to bear two odor absorption surfaces 108, one on each side of the sheet material 710. Thus, the carrier structure 104 described in FIG. 7 has an 'S' shaped profile with a structure having a cross section with a solid base bearing two absorption surfaces on either side.

Figure 8:
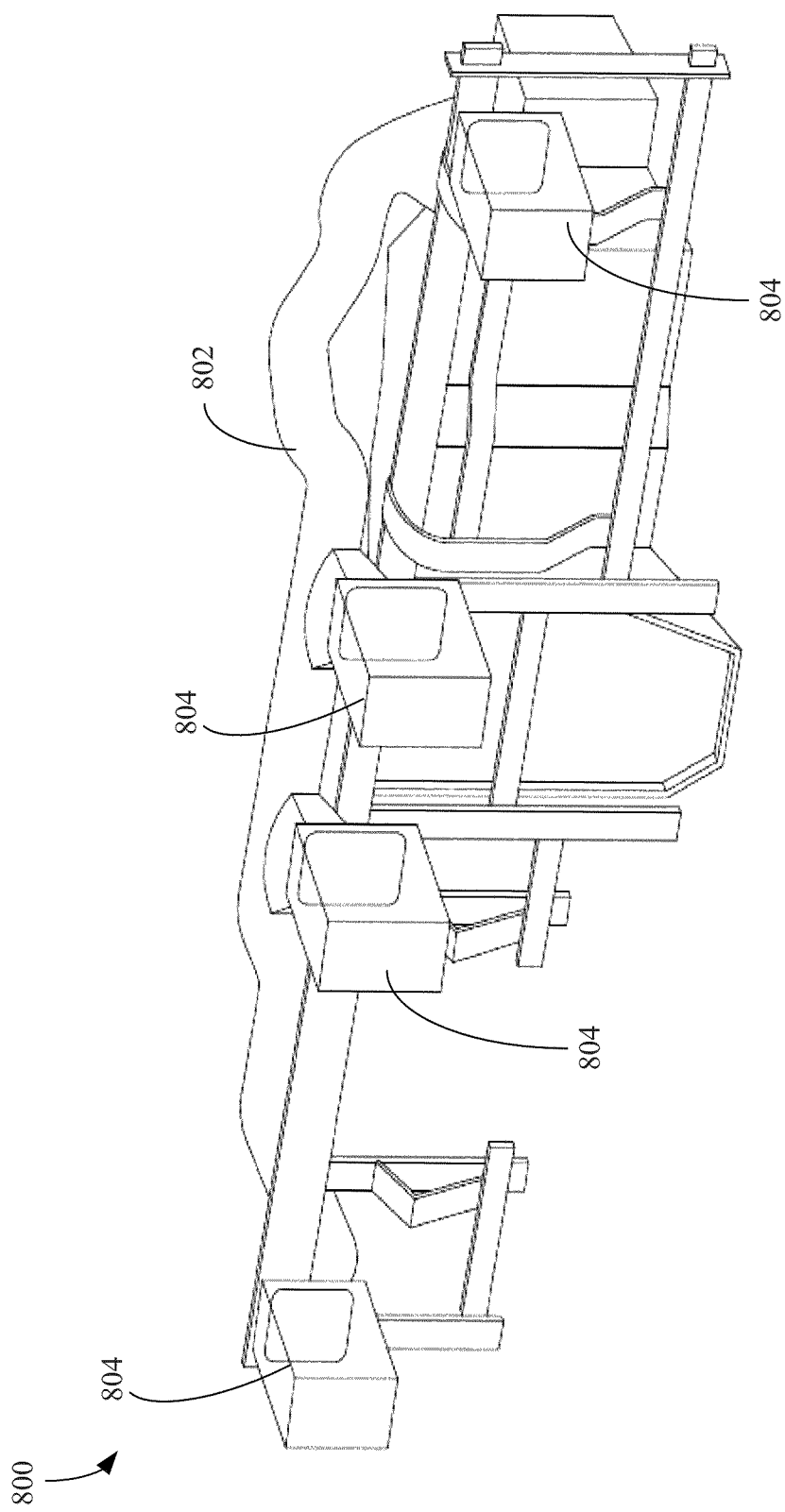
FIG. 8 shows a schematic diagram of a vehicle air duct system in accordance with an embodiment of the invention.

FIG. 8 shows a partial schematic diagram of a vehicle air circulation system 800 that can incorporate therein one or more absorption components 100 in accordance with one or more aspects as detailed herein. The vehicle circulation system 800 as shown herein comprises means for supplying air to the vehicle interior such as an air duct 802 with about four air outlets 804 that circulate air into the vehicle interior. Generally, such outlets 804 are included in the vehicle cockpit located in the front portion of the vehicle interior as shown in FIG. 8 and/or in the side walls or other suitable locations (not shown) throughout the vehicle interior. Means for odor absorption, such as the absorption component 100 as described in accordance with the various aspects detailed herein, can be incorporated in the circulation system 800 at such outlets 804 and/or it may be incorporated at the inlets (not shown) that pump fresh air into the passenger compartment of the vehicle. Alternately, the absorption component 100 may be located at any intermediate position between the inlet and the outlet 804. Thus, the absorption component 100 which comprises means for carrying fabric coated with an odor absorbing deodorant, such as the carrier structure 104, when placed parallel to the air flow, deodorizes air while facilitating better air circulation in the vehicle interior, as it does not impede air flow thereby providing improved comfort to the passengers in the vehicle.

It may be appreciated that although the use of an absorption component 100 in accordance with different aspects is described with respect to the air circulation system 800 for a vehicle, such an absorption component 100 can be used in other fluid circulation systems that necessitate efficient odor absorption without obstruction of the fluid flow. In addition, the carrier structures 104 may also bear other coating/filtering materials such as, anti-bacterial coatings, etc., and may be placed in line with the air flow thereby facilitating filtering of air without reducing the air pressure or velocity.

Although preferred embodiments of the invention are disclosed for illustrative purposes, those skilled in the art will appreciate that many additions, modifications, and substitutions are possible without departing from the scope and spirit of the invention.

The invention claimed is:

1. A deodorizing system, comprising:
   a channel housing including a plurality of walls defining respective interior surfaces forming an air duct, at least one of the plurality of walls including an aperture; and
   at least one absorption component that absorbs odors from a fluid flowing through the air duct of the channel housing, wherein:
   the absorption component comprises at least one absorption surface that extends in a longitudinal direction, covers the aperture, and forms at least part of at least one of the interior surfaces of the air duct; and
   the absorption component is oriented with respect to the channel housing such that the longitudinal direction of the at least one absorption surface is substantially parallel to the fluid flow.

2. The deodorizing system of claim 1, wherein the absorption component comprises at least one carrier structure bearing the absorption surface thereon.

3. The deodorizing system of claim 2, wherein a minimum quantum of surface area of the absorption surface is transverse to the fluid flow.

4. The deodorizing system of claim 2, wherein the absorption surface comprises a deodorant fabric impregnated with an odor absorbing coating.

5. The deodorizing system of claim 4, wherein the deodorant fabric is at least one of molded into or bonded to the carrier structure.

6. The deodorizing system of claim 2, wherein the carrier structure comprises at least a foam seal that facilitates adhering the carrier structure to the channel housing.

7. The deodorizing system of claim 2, wherein the carrier structure is affixed to the channel housing such that fluid particles at a periphery of the fluid flow are in physical contact with the absorption surface.

8. The deodorizing system of claim 7, wherein the carrier structure is affixed to the channel housing such that a plane of the absorption surface that is in contact with the fluid flow is flush with an inner surface of the channel housing.

9. The deodorizing system of claim 7, wherein the absorption component comprises a plurality of carrier structures affixed to a plurality of sides of the channel housing, the carrier structures are interconnected to each other creating a band that surrounds at least a portion of the fluid flow within the channel housing such that only one absorption surface of each of the carrier structures is in physical contact with the fluid flow.

10. The deodorizing system of claim 9, wherein the channel housing includes at least one aperture through each wall and the plurality of carrier structures cover the apertures such that the fluid contacts the absorption surface of the plurality of carrier structures.

11. The deodorizing system of claim 7, wherein the carrier structure is a continuous sheet of material with the absorption surface configured on one side of the sheet.

12. The deodorizing system of claim 2, wherein the carrier structure is configured as a frame with an aperture and the at least one absorption surface is configured as a deodorant fabric covering the aperture of the frame.

13. The deodorizing system of claim 2, wherein the carrier structure is a molded plastic frame.

14. The deodorizing system of claim 13, wherein the molded plastic frame has a shape selected from one or more of planar, arcuate, circular and combinations thereof.

15. A deodorizing system, comprising:
   an air duct that supplies air to a vehicle interior, the air duct being formed from a plurality of walls defining respective interior surfaces of the air duct, at least one of the plurality of walls including an aperture; and
   at least one odor absorption filter comprising at least one odor absorption surface extending in a longitudinal direction along a length of the filter and the filter covers the aperture such that the longitudinal direction is parallel to air flow within the air duct,
   wherein the at least one absorption surface forms at least part of at least one of the interior surfaces of the air duct.

16. The deodorizing system of claim 15, wherein the at least one filter is arranged within the air duct such that the at least one odor absorption surface is in physical contact with the air flow.

17. The deodorizing system of claim 15, wherein the filter comprises at least one carrier structure bearing the odor absorption surface thereon.

18. The deodorizing system of claim 17, wherein the odor absorption surface includes a deodorant coated fabric.

19. The deodorizing system of claim 17, wherein the carrier structure comprises one or more connection elements that facilitate connecting the carrier structure to at least one other carrier structure.

20. The deodorizing system of claim 17, wherein the carrier structure is configured to have one or more of planar, arcuate and circular shapes.

21. The deodorizing system of claim 15, wherein the filter is arranged at one or more of an inlet or outlet of the air duct.

22. The deodorizing system of claim 15, wherein the filter is configured such that a first part of the air filter is away from a path of the air flow and a second part of the air filter is in the path of the air flow.

23. A deodorizing system for a vehicle comprising:
   means for supplying air to a vehicle interior, including a plurality of walls defining respective interior surfaces for channeling the air, at least one of the plurality of walls including an aperture;
   means for absorbing odors comprising at least one odor absorbing surface that extends in a longitudinal direction along a length of the means for absorbing odors; and
   the means for absorbing odors is arranged to cover the aperture such that the at least one odor absorbing surface is in contact with the air flow and the longitudinal direction is parallel to a direction of air flow, wherein the at least one absorption surface forms at least part of at least one of the interior surfaces of the means for supplying air.

24. The deodorizing system of claim 23, wherein the means for absorbing odors is arranged such that the means for absorbing odors is away from a path of the air flow and only the at least one odor absorbing surface is in physical contact with the air flow.

25. The deodorizing system of claim 23, wherein the means for absorbing odors is arranged such that the means for absorbing odors is in a path of the air flow.

26. The deodorizing system of claim 23, wherein the means for absorbing odors further comprises means for bearing the odor absorbing surface thereon.

* * * * *